(12) United States Patent
Yamada et al.

(10) Patent No.: US 8,327,804 B2
(45) Date of Patent: Dec. 11, 2012

(54) MEASUREMENT OBJECT HOLDER, LIVING BODY HOLDER, AND OPTICAL MEASUREMENT INSTRUMENT

(75) Inventors: Yukio Yamada, Tokyo (JP); Hitoshi Shimizu, Kanagawa (JP); Takeshi Kimura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1 day.

(21) Appl. No.: 13/146,921

(22) PCT Filed: Feb. 1, 2010

(86) PCT No.: PCT/JP2010/051347
§ 371 (c)(1),
(2), (4) Date: Jul. 29, 2011

(87) PCT Pub. No.: WO2010/087477
PCT Pub. Date: Aug. 5, 2010

(65) Prior Publication Data
US 2012/0017842 A1    Jan. 26, 2012

(30) Foreign Application Priority Data

Jan. 30, 2009 (JP) ................. 2009-020331
Jan. 25, 2010 (JP) ................. 2010-013232

(51) Int. Cl.
*A01K 29/00* (2006.01)
(52) U.S. Cl. ............... 119/421; 119/417; 119/755
(58) Field of Classification Search .......... 119/421, 119/416, 417, 427, 751, 755, 752, 756; 128/845, 128/869, 870
See application file for complete search history.

(56) References Cited

U.S. PATENT DOCUMENTS

| | | | | |
|---|---|---|---|---|
| 1,956,499 A * | 4/1934 | Dworetzky | ......... | 119/729 |
| 3,300,040 A * | 1/1967 | Ferguson | ......... | 206/457 |
| 3,428,030 A * | 2/1969 | Updegraff | ......... | 119/752 |
| 3,776,375 A * | 12/1973 | Rohdin | ......... | 206/459.5 |
| 5,320,069 A * | 6/1994 | Anderson et al. | ......... | 119/751 |
| 6,675,741 B2 * | 1/2004 | Remmler | ......... | 119/755 |
| 7,146,936 B2 * | 12/2006 | Dazai et al. | ......... | 119/756 |
| 7,784,429 B2 * | 8/2010 | Chiodo | ......... | 119/417 |

(Continued)

FOREIGN PATENT DOCUMENTS
JP    7-111999 A    5/1995
(Continued)

OTHER PUBLICATIONS

IEEE Transaction on Medical Imaging, vol. 23, No. 4, Apr. 2004, p. 401-412 "Iterative Tomographic Image Reconstruction Using Fourier-Based Forward and Back-Projectors".

(Continued)

*Primary Examiner* — Yvonne Abbott
(74) *Attorney, Agent, or Firm* — SOLARIS Intellectual Property Group, PLLC

(57) ABSTRACT

A measurement object holder that holds a measurement object in an optical measurement instrument, wherein the optical measurement instrument takes, as the measurement object, a living body in which isotropic scattering of light occurs inside and receives light emitted from the measurement object is disclosed. The measurement object holder includes a block that is formed in a predetermined outer shape by a material having optical properties in which the isotropic scattering of light occurs inside; and a cavity portion that is formed inside the block, that has an inner shape following the outer shape of the measurement object and in which the measurement object is accommodated.

10 Claims, 10 Drawing Sheets

U.S. PATENT DOCUMENTS

| | | | |
|---|---|---|---|
| 8,218,148 B2 * | 7/2012 | Arnz | 356/445 |
| 2003/0136354 A1 * | 7/2003 | Remmler | 119/755 |
| 2004/0015062 A1 | 1/2004 | Ntziachristos et al. | |
| 2009/0247882 A1 | 10/2009 | Tojo | |

FOREIGN PATENT DOCUMENTS

| | | |
|---|---|---|
| JP | 11-173976 A | 7/1999 |
| JP | 2004-514150 T | 5/2004 |
| JP | 2006-026017 A | 2/2006 |
| JP | 2009-236847 A | 10/2009 |

OTHER PUBLICATIONS

IEEE Transaction on Medical Imaging, vol. 23, No. 4, Apr. 2004, p. 492-500 "Experimental Fluorescence Tomography of Tissues With Noncontact Measurements".

Optics & Photonics Japan 2009, p. 436-437, Nov. 24, 2009.

* cited by examiner

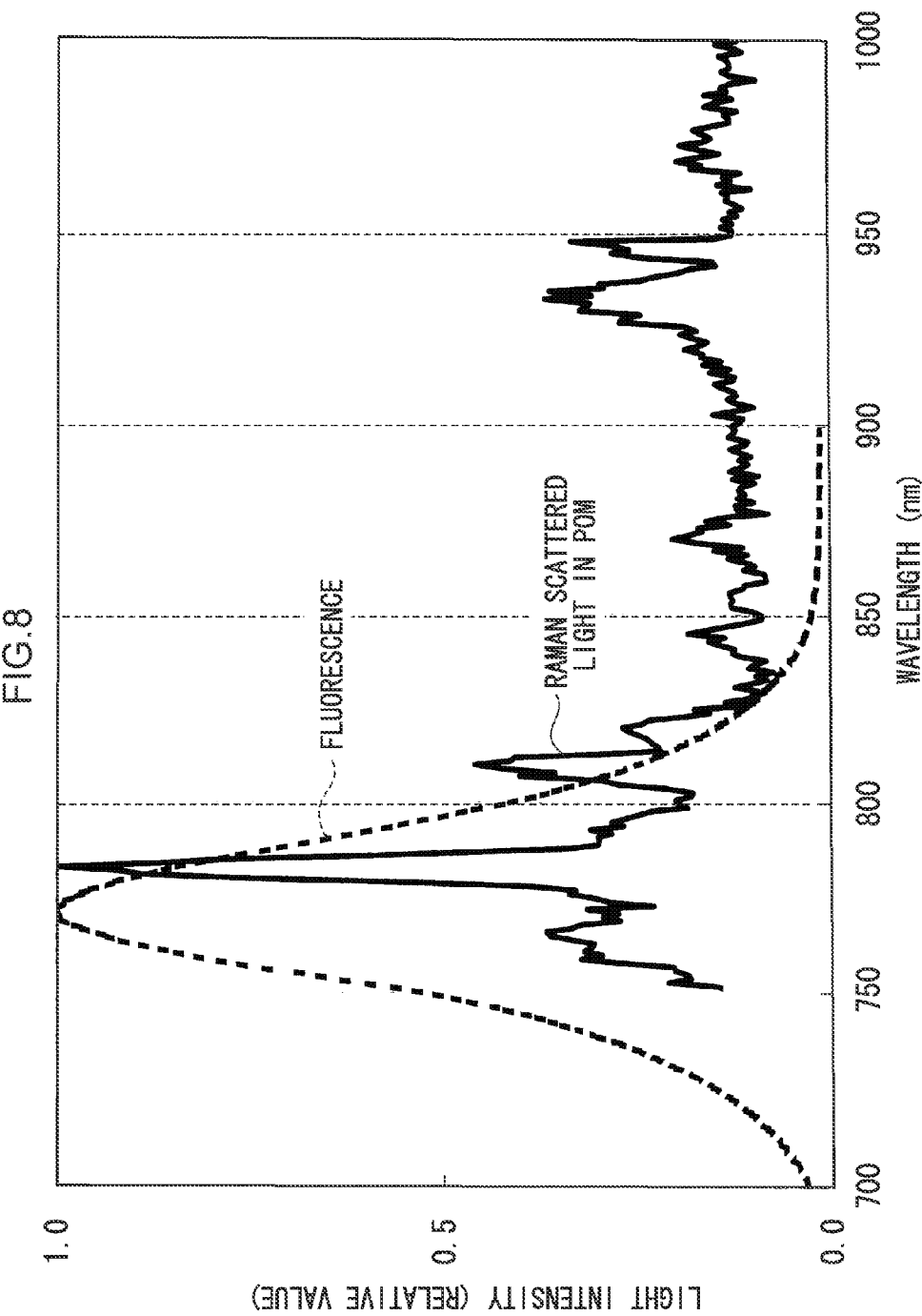

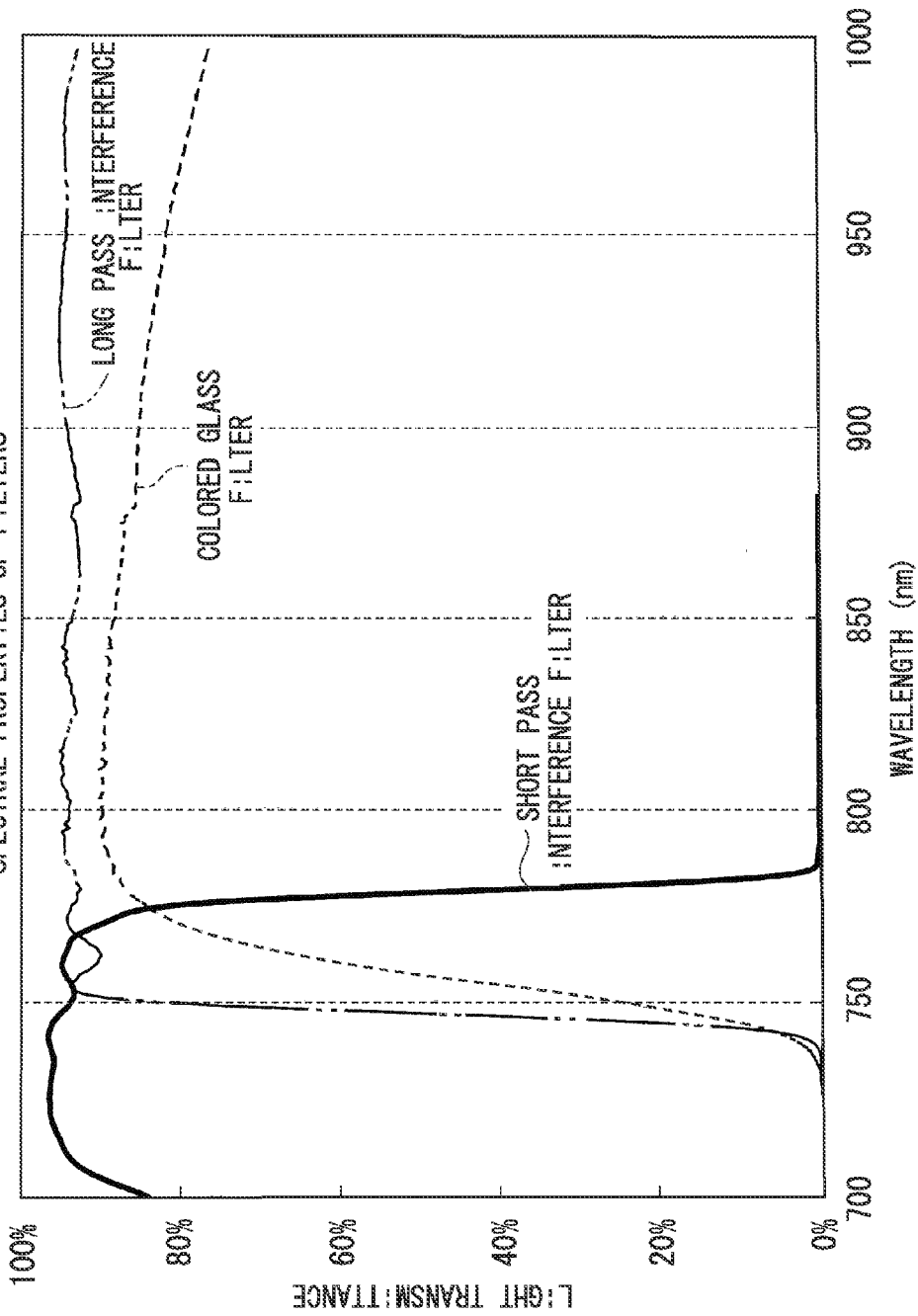

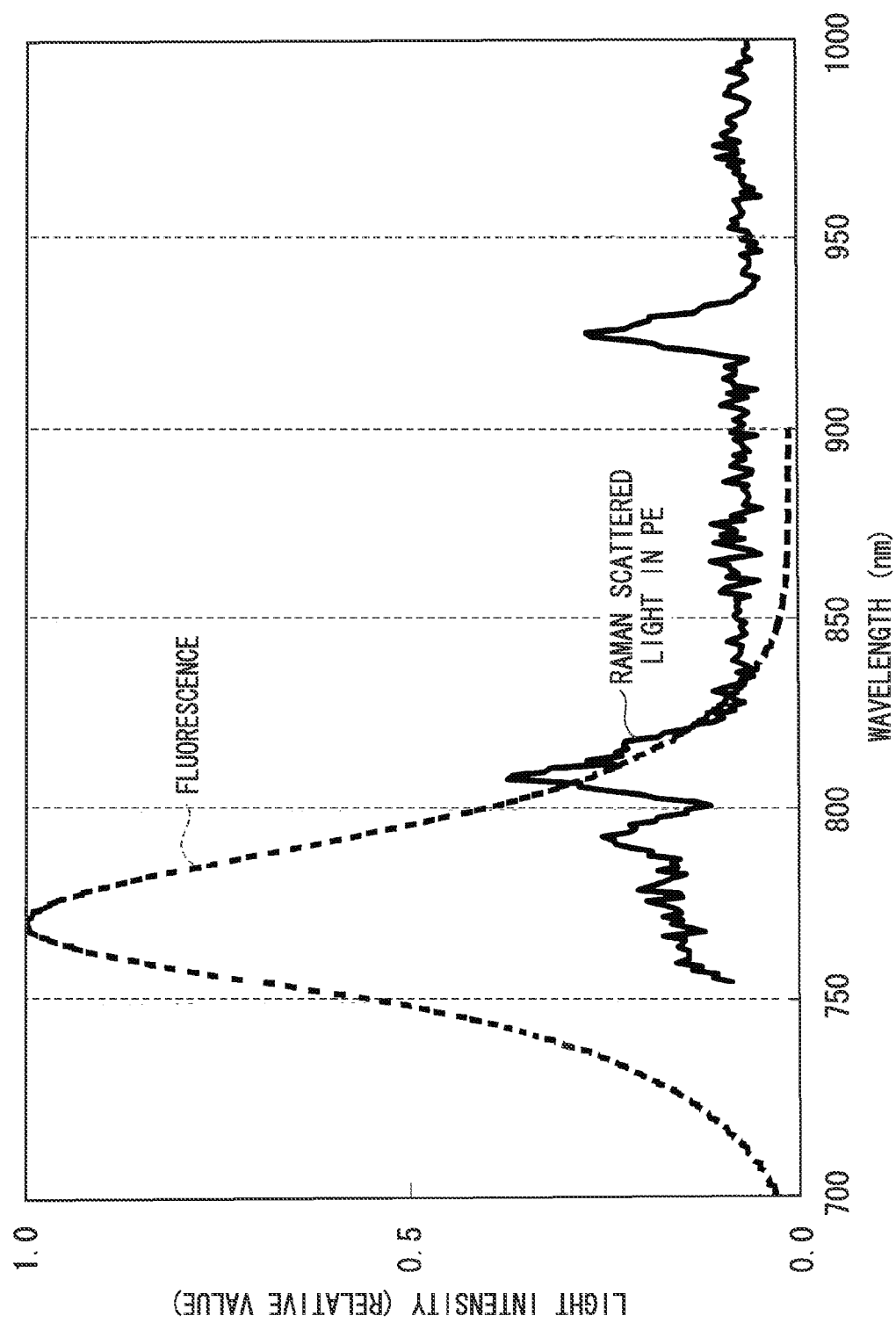

MEASUREMENT OBJECT HOLDER, LIVING BODY HOLDER, AND OPTICAL MEASUREMENT INSTRUMENT

TECHNICAL FIELD

The present invention pertains to tomography using light and specifically relates to a measurement object holder, a living body holder, and an optical measurement instrument which, hold a measurement object when taking a living body such as a small animal as the measurement object.

BACKGROUND ART

Methods of capturing tomographic images taking a living body as a measurement object include X-ray computerized tomography (CT) using X-rays, ultrasound CT using ultrasound, NMR-CT using nuclear magnetic resonance, and proton CT using a particle beam of protons or the like.

Meanwhile, optical tomography (called optical CT below) can be applied to the tomographic observation of small animals because living body tissue transmits light of predetermined wavelengths such as near-infrared light.

When a living body is irradiated with light, the light passes through the living body while scattering isotropically; thereby, light corresponding to the light with which the living body has been irradiated is emitted from around the living body. Based on this, in optical CT, a living body that is a measurement object is irradiated with light of a predetermined wavelength, and the intensity of the light transmitted through the measurement object and radiating around it is detected. Further, in optical CT, by changing the positions of irradiation with the light and receiving the emitted light, measurement information that is the basis of tomographic information (optical tomographic information) of the measurement object can be acquired.

Within a living body or the like, in contrast to within air and so forth in which the straightness of light can be ensured, light scattering and absorption occur. For this reason, in order to obtain adequate tomographic information of a living body, it is necessary to adequately grasp the outer shape of the measurement object.

For example, Non-Patent Document 1 proposed three-dimensionally measuring of the shape of a measurement object beforehand, and Patent Document 1 proposes filling a container with a solution whose optical properties, such as its absorption coefficient and its scattering coefficient with respect to light, substantially coincide with those of the measurement object, immersing the measurement object in this solution, and acquiring tomographic information including the container.

Non-patent Document 1: IEEE Transaction on Medical Imaging, Vol. 23, No. 4, April 2004
Patent Document 1: JP-A No. 11-173976

DISCLOSURE OF INVENTION

Technical Problem

In these conventional methods, because the outer shape of a measurement object can be made known, adequate tomographic information including a living body that is a measurement object can be obtained. Yet with these methods, work such as performing a three-dimensional measurement and replacing the solution each time a measurement with respect to one living body is performed is necessary. For this reason, when performing a measurement in regard to numerous living bodies, an enormous amount of labor and time becomes necessary.

Meanwhile, in order to obtain tomographic information of a living body, it is necessary to hold the living body in a fixed state, irradiate the living body with light at predetermined intervals around the living body, and receive the light that has been emitted from the living body at each of the positions of irradiation. At this time, if the living body moves while data corresponding to one circumnavigation around the living body are acquired, adequate tomographic information cannot be obtained and certain processes for dealing with this will be necessary, such as redoing the measurement. Therefore, an anesthetic is administered to the living body and a measurement is performed in a state where the movement of the living body has been stopped.

However, when an anesthetic is administered to the living body, the muscles of the living body relax. For this reason, the organs and so forth inside the living body would not be held in their original positions and adequate tomographic information cannot be obtained.

For example, when immersing a living body in a container having substantially same optical properties and performing a measurement, in order to keep the living body in an alive state it is necessary to immerse the torso region and below in the solution such that the living body is suspended in a state while the head region of the living body sticks out from the solution. In this state, however, if an anesthetic has been administered to the living body, the organs inside the body of the living body move downward and it is difficult to grasp their origin positions.

The present invention has been made in light of the above-described facts, and an object thereof is to provide a measurement object holder, a living body holder, and an optical measurement instrument with which the acquisition of adequate tomographic information is easy when a living body has been taken as a measurement object.

Solution to Problem

A measurement object holder of the present invention for achieving the above-described object is a measurement object holder that holds a measurement object in an optical measurement instrument, wherein the optical measurement instrument takes, as the measurement object, a living body in which isotropic scattering of light occurs inside and receives light emitted from the measurement object, the measurement object holder including: a block that is formed in a predetermined outer shape by a material having optical properties in which the isotropic scattering of light occurs inside; and a cavity portion that is formed inside the block, that has an inner shape following the outer shape of the measurement object and in which the measurement object is accommodated.

According to this invention, the cavity portion having the inner shape in conformity with and follows the outer shape of the measurement object is formed inside the block having a predetermined outer shape. It is preferable for the cavity portion to be slightly smaller than the size of the measurement object, for example, so that the measurement object is slightly compressed when the measurement object has been accommodated in the cavity portion and so that the epidermis of the measurement object is accustomed to the cavity portion and the surface of the measurement object closely contacts with the inner surface of the cavity portion. Thereby, the measurement object is accommodated and retained in a state while its original shape is maintained.

Further, the block is formed by a material having optical properties in which the scattering of light becomes isotropic (called "isotropic scattering" below) in an area beyond a light penetration length and in which the isotropic scattering can be considered as being substantially continued even inside the measurement object as a result of the measurement object being in contact with the inner surface of the block inside the cavity portion.

Because of this, measurement error can be reduced when performing a measurement for obtaining optical tomographic information of a living body that is a measurement object using light. Further, the measurement object can be prevented from moving when performing a measurement for obtaining optical tomographic information (data) with respect to the measurement object, and even in a state in which the measurement object has relaxed, the measurement object can be prevented from losing its outer shape and the organs and so forth inside the measurement object can be held close to their original positions.

Further, in the measurement object holder of the present invention, the block is formed in a cylindrical shape, and the cavity portion is formed such that a length direction of the measurement object is along an axial direction of the block.

According to the above invention, the outer shape of the block is formed in a cylindrical shape. Therefore, the outer shape of the block does not change when a light source and a light receiving element have been relatively moved in the body length direction with respect to the measurement object.

Further, in the measurement object holder of the present invention, the block is divided into plural sections in a plane passing through the cavity portion.

According to the above invention, recessed portions forming the cavity portion are opened by dividing the block, and the accommodation and removal of the measurement object inside and from the recessed portions, that is the cavity portion, is easy. Thereby, the workability of measurement with respect to the measurement object can be improved. It is preferable for the division of the block to be in a plane along the body length direction of the measurement object.

Further, in the measurement object holder of the present invention, it suffices for the cavity portion to be formed so as to at least accommodate a site set as a measurement site in the measurement object.

A living body holder to which the above-describe present invention is applied includes a block that is formed in a predetermined outer shape by a material having optical properties in which isotropic scattering of light occurs inside, the block being formed with a cavity portion inside the block having an inner shape that follows an outer shape of a living body in which isotropic scattering of light occurs inside, and the living body being held in the block by the living body being accommodated inside the cavity portion.

Further, in the living body holder of the present invention, the block is formed in a cylindrical shape, and the cavity portion is formed such that an axial direction of the block is along a length direction of the living body, and it is preferable for the block is divided into plural sections by a plane passing through the cavity portion.

An optical measurement instrument to which the present invention is applied may include: the living body holder that accommodates a living body to which has been administered a fluorescent substance that emits fluorescence as a result of being irradiated with excitation light; holding portions that hold, at both end portions in a length direction of the living body, the block of the living body holder in which the living body is accommodated; a light source head that irradiates, with the excitation light, the living body inside the block held by the holding portions; and a light receiving head that receives the fluorescence emitted from the fluorescent substance inside the living body due to the irradiation of the excitation light from the light source head.

In the optical measurement instrument, the block of the living body holder and the living body can be regarded as being integrated and the light emitted from the living body can be measured.

Further, in the optical measurement instrument of the present invention, a wavelength of the excitation light, the fluorescent substance, and the material of the block are set such that a wavelength of the fluorescence and a local maximum of a wavelength of Raman scattered light differ by a predetermined wavelength or more, on the basis of the wavelength of the excitation light determined per fluorescent substance, the wavelength of the fluorescence, and the wavelength of the Raman scattered light emitted from the block due to the Raman effect occurring inside the block as a result of the block being irradiated with the excitation light.

In a case where a block that transmits light has been irradiated with light, Raman scattered light resulting from the Raman effect is generated. If the wavelength of this Raman scattered light is within the wavelength received by the light receiving head, error arises in the quantity of light received by the light receiving head.

Further, the peak wavelength of the Raman scattered light shifts depending on the material of the block and the wavelength of the excitation light that is the light with which the block is irradiated. That is, by changing the wavelength of the excitation light, the peak wavelength of the Raman scattered light changes, and by changing the material of the block without changing the wavelength of the excitation light, the peak wavelength of the Raman scattered light also changes.

Therefore, measurement error caused by the Raman scattered light can be controlled by appropriately setting the fluorescent substance (the wavelength of the excitation light and the wavelength of the fluorescence) and the material of the block such that the wavelength of the fluorescence and the wavelength taking the local maximum of the Raman scattered light are separated (different by) a predetermined length or more.

In this case, the predetermined wavelength separating the wavelength of the fluorescence and the local maximum of the wavelength of the Raman scattered light can be a wavelength determined based on the spectral properties of an optical filter disposed in the light receiving head. Thereby, the optical filter disposed in the light receiving head can prevent noise caused by the Raman scattered light from ending up being measured.

At this time, the block may be formed by a material determined on the basis of the wavelength of the excitation light and the wavelength of the fluorescence, or depending on the material of the block, the fluorescent substance administered to the living body, the wavelength of the excitation light with which the living body is irradiated from the light source head, and the wavelength of the fluorescence received by the light receiving head may be changed.

Advantageous Effects of Invention

As described above, the measurement object holder and the living body holder of the present invention can retain a living body taken as a measurement object while maintaining the outer shape of the living body and the original positions of the organs in a held state, and accurate measurement for obtaining optical tomographic information is easy.

Further, in the measurement object holder and the living body holder of the present invention, the accommodation and removal of a living body taken as a measurement object can be performed rapidly and smoothly; therefore, smooth measurement when obtaining adequate optical tomographic information is possible.

Further, in the optical measurement instrument of the present invention, measurement error due to Raman scattered light is controlled and measurement data which enables high-precision tomographic image reconstruction can be obtained.

BRIEF DESCRIPTION OF DRAWINGS

FIG. 8 is a diagram showing spectral properties of Raman scattered light in polyacetal resin (POM) and fluorescence with respect to excitation light whose wavelength is 730 nm.

FIG. 9 is a diagram showing an example of spectral properties of optical filters that are applicable to the present embodiment.

FIG. 10 is a diagram showing spectral properties of Raman scattered light in polyethylene (PE) and fluorescence with respect to excitation light whose wavelength is 730 nm.

BEST MODE FOR CARRYING OUT THE INVENTION

Figure 3:
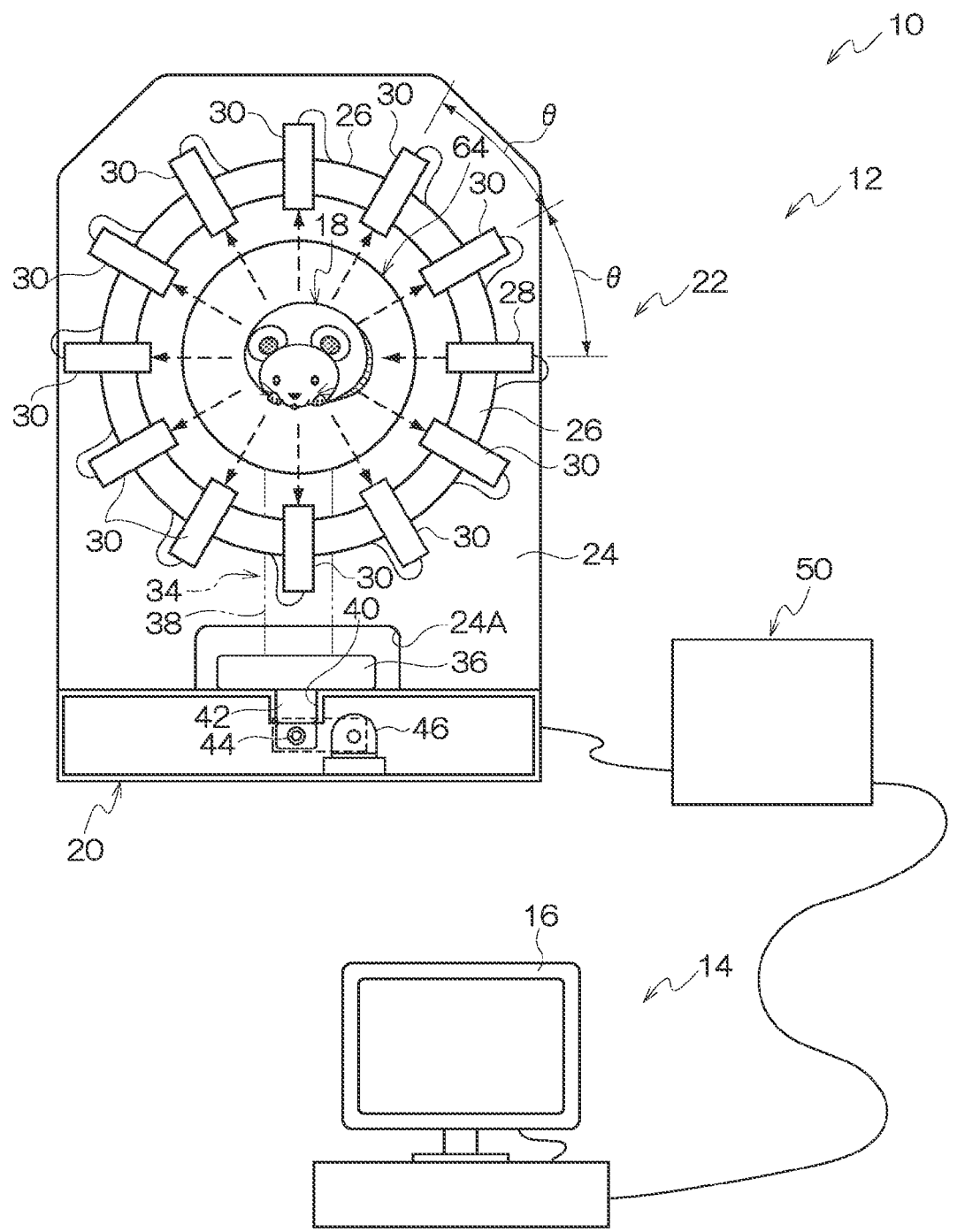
FIG. 3 is a schematic configuration diagram of an optical tomographic measurement instrument pertaining to the present exemplary embodiment.

A mode of carrying out the present invention will be described below with reference to the drawings. FIG. 3 shows the schematic configuration of an optical tomographic measurement instrument 10 pertaining to the present exemplary embodiment and which serves as an example of an optical measurement instrument. The optical tomographic measurement instrument 10 is formed to include a measurement section 12 and an image processing section 14 that performs tomographic reconstruction on the basis of electric signals that have been outputted from the measurement section 12. In the image processing section 14, a CRT or LCD monitor 16 is disposed as a display component (a display device).

The optical tomographic measurement instrument 10 applied to the present embodiment takes a living body, such as a small animal like a nude mouse, for example, as a measurement object (called a specimen 18 below) and irradiates the specimen 18 with light of a predetermined wavelength (e.g., near-infrared light). The light with which the specimen 18 has been irradiated passes through the specimen 18 while scattering inside the specimen 18, and light corresponding to this light with which the specimen 18 has been irradiated is emitted around the specimen 18. The optical tomographic measurement instrument 10 changes the position at which it irradiates the specimen 18 with the light, detects the light (light intensity) emitted from the specimen 18 at each of the positions of irradiation, and performs predetermined data processing with respect to these detection results. The optical tomographic measurement instrument 10 displays on the monitor 16 an image corresponding to optical tomographic information (data) of the specimen 18 obtained from these measurement results.

Further, by administering a material or drug (a fluorescent labeling agent or the like) including a fluorescent substance to the specimen 18 and irradiating the specimen 18 with excitation light with respect to this fluorescent substance, fluorescence corresponding to the concentration distribution of the fluorescent substance inside the specimen 18 is emitted from around the specimen 18. The optical tomographic measurement instrument 10 detects the fluorescence and performs predetermined data processing (image processing) to thereby obtain distribution information including the concentration distribution of the fluorescent substance (the intensity distribution of the fluorescence) as tomographic information.

The optical tomographic measurement instrument 10 may also generate an image of the distribution information of the fluorescent substance and may enable to display the distribution information as optical tomographic information of the specimen 18. An embodiment will be described below, as an example, in which a fluorescent substance (not shown) that emits fluorescence as a result of being irradiated with light of a predetermined wavelength (called excitation light below) is administered to the specimen 18, and in which the concentration distribution of the fluorescent substance in the specimen 18 is acquired to enable observation of the movement, accumulation process, and so forth of the fluorescent substance in the specimen 18.

Figure 4:
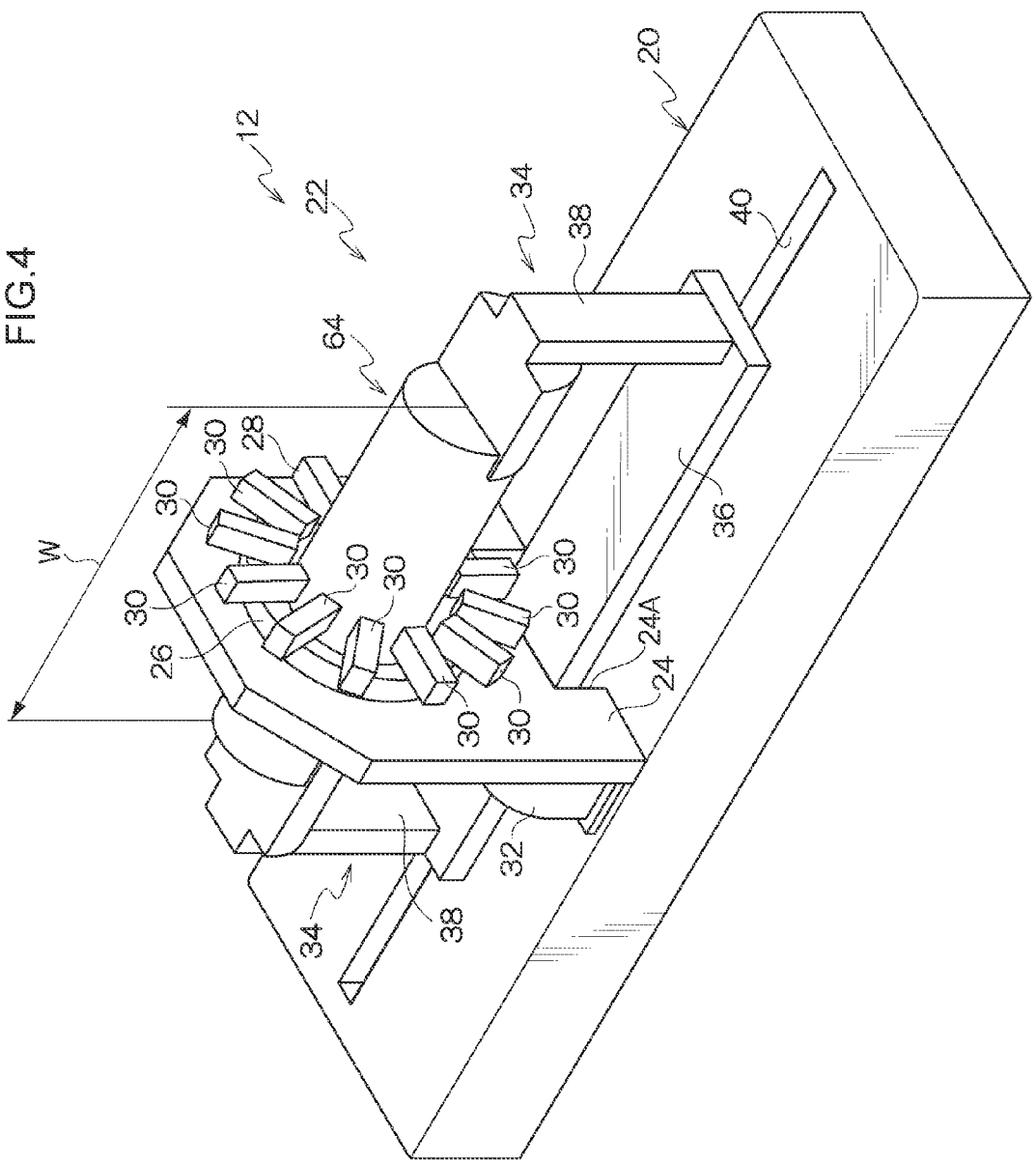
FIG. 4 is a schematic perspective view of main portions showing an example of a measurement unit.

As shown in FIG. 3 and FIG. 4, in the measurement section 12, a measurement unit 22 is disposed on a mount 20. The measurement unit 22 is equipped with a plate-shaped base 24 that is disposed upright on the mount 20, and a ring-shaped frame 26 is placed on one face of the base 24.

On the frame 26, a light source head 28 that emits the excitation light and multiple light receiving heads 30 that receive the fluorescence emitted from the specimen 18 are placed at predetermined angular intervals radially about the axial center of the frame 26. The light source head 28 and the light receiving heads 30 are placed such that the angular intervals between the light source head 28 and the light receiving heads 30 adjacent to the light source head 28 and the angular intervals between the light receiving heads 30 adjacent to each other are equal at an angle θ. In the present embodiment, as an example, eleven of the light receiving heads 30 are disposed and the angle θ is 30° (θ=30°).

In the optical tomographic measurement instrument 10, the specimen 18 is placed in the axial center portion of the frame 26 of the measurement unit 22. An open portion is formed coaxially with the frame 26 in the base 24, and the specimen 18 is relatively moved along the axial direction of the frame 26.

In the measurement unit 22, the frame 26 is attached to the base 24 so as to be rotatable about its axial center. Further, a rotating motor 32 is attached to the mount 20, and when the rotating motor 32 is driven, the frame 26 is rotated with its axial center serving as its center of rotation.

Because of this, the optical tomographic measurement instrument 10 can move around the specimen 18 the positions at which it irradiates the specimen 18 with the excitation light emitted from the light source head 28 and can simultaneously receive the fluorescence with each of the light receiving heads 30 at each of the positions of irradiation.

The optical tomographic measurement instrument 10 performs measurements while relatively rotating the frame 26 with respect to the specimen 18 in 30° steps, for example. An arbitrary mechanism can be used for the rotating mechanism of the frame 26. In the present embodiment, the optical tomographic measurement instrument 10 is described as relatively rotating the specimen 18 and the frame 26. However, the optical tomographic measurement instrument 10 is not limited to this and, for example, a configuration may be applied in which measurement heads having the functions of the light source head 28 and the light receiving heads 30 integrated therein are used, and these measurement heads are attached at predetermined angular intervals to the frame 26.

As shown in FIG. 4, a pair of arms 34 are disposed, as holding portions that hold the specimen 18, in the optical tomographic measurement instrument 10. The arms 34 are placed a predetermined interval apart from each other, with the base 24 of the measurement unit 22 being interposed therebetween.

Further, a strip-like slide plate 36 is placed on the mount 20. A rectangular-shaped open portion 24A is formed in the end portion of the base 24 on the mount 20 side. The slide plate 36 is placed with its lengthwise direction along the axial direction of the frame 26 and is inserted through the open portion 24A of the base 24. Further, props 38 of the arms 34 are attached to both lengthwise direction end portions of the slide plate 36; thereby, the pair of arms 34 are held on the mount 20 in a state in which they are a fixed interval apart from each other.

As shown in FIG. 3 and FIG. 4, a guide groove 40 is formed in the mount 20 along the lengthwise direction. As shown in FIG. 4, a leg portion 42 conforming to the open width of the guide groove 40 is attached to the slide plate 36, and the leg portion 42 is inserted into the guide groove 40. Thereby, in the measurement section 12, the slide plate 36 is movable on the mount 20 along the axial direction of the frame 26.

Further, a feed screw 44 and a moving motor 46 that drives the feed screw 44 to rotate are disposed inside the mount 20. The leg portion 42 inserted through the guide groove 40 is screwed onto the feed screw 44. Thus, in the measurement section 12, when the feed screw 44 is rotated by the driving of the moving motor 46, the slide plate 36 moves along the guide groove 40. In the measurement section 12, the pair of arms 34 holding the specimen 18 are moved, by this movement of the slide plate 36, along the axial direction of the frame 26 in a state in which the fixed interval is maintained.

Figure 5:
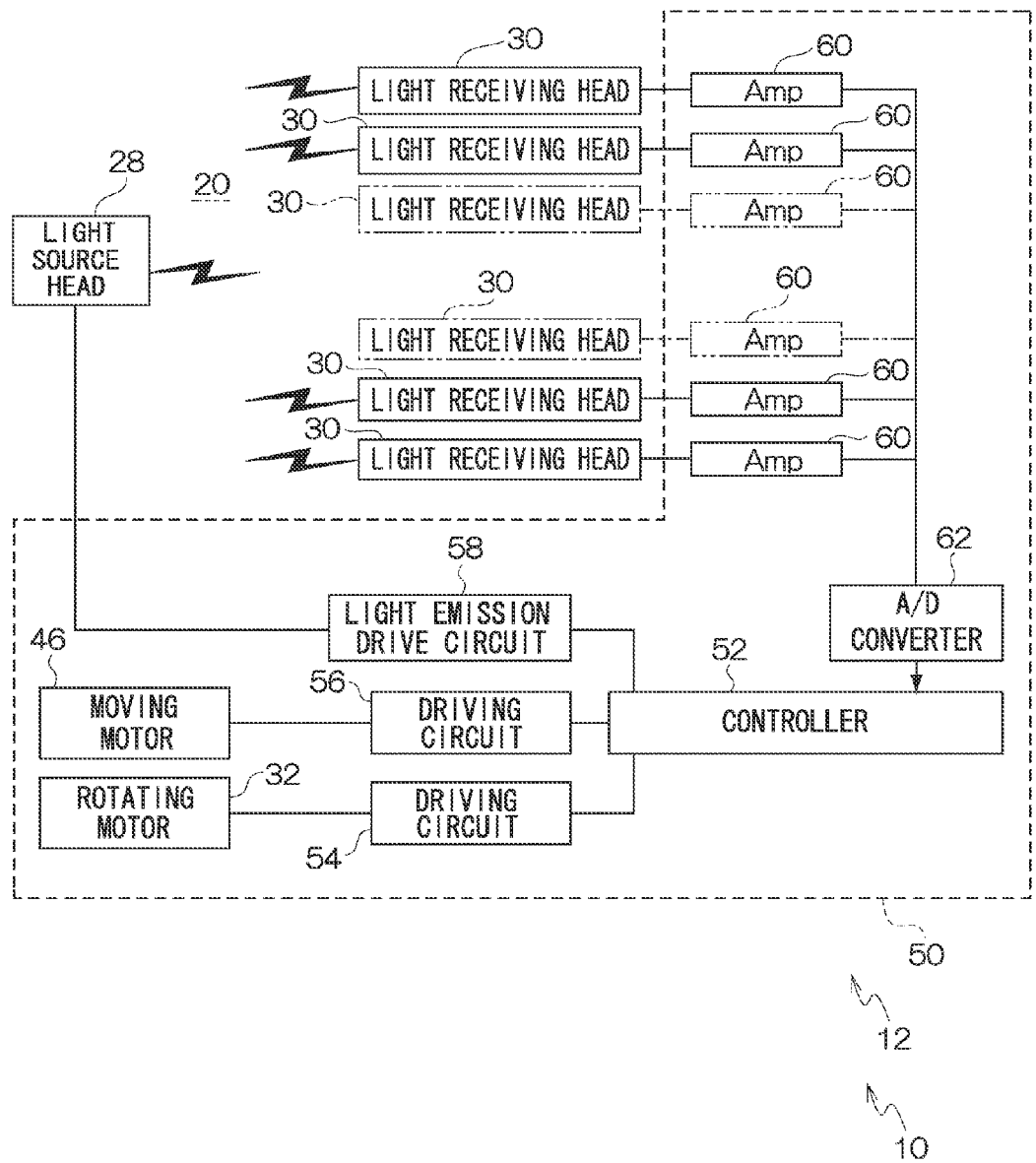
FIG. 5 is a schematic configuration diagram of a control unit disposed in a measurement section.

FIG. 5 shows the schematic configuration of a control unit 50 that controls the operation of the measurement section 12. A controller 52 equipped with a microcomputer including a CPU, a ROM, a RAM, and the like is disposed in the control unit 50. The controller 52 operates and performs various controls on the basis of a program that is stored beforehand therein or a program that is inputted thereto via a recording medium.

A drive circuit 54 that drives the rotating motor 32 and a drive circuit 56 that drives the moving motor 46 are disposed in the control unit 50, and these are connected to the controller 52. The controller 52 controls the operation of the drive circuits 54 and 56 in order to control the angle of rotation of the frame 26 driven by the rotating motor 32, and control the position of the pair of arms 32, that is, the position of the specimen 18 with respect to the frame 26 (the light source head 28 and the light receiving heads 30), driven by the moving motor 46. As the rotating motor 32 and the moving motor 46, it is preferable to use pulse motors with which it is easy to determine angle and position, but arbitrary motors can be used as long as the drive quantity is adequately controllable.

A light emission drive circuit 58 that drives the light source head 28 is disposed in the control unit 50, and the light emission drive circuit 58 is connected to the controller 52. Further, amplifiers (amps) 60 that amplify electric signals output from the light receiving heads 30 and an A/D converter 62 that converts the amplified electric signals into digital signals are disposed in the control unit 50.

The controller 52 sequentially converts the electric signals output from the light receiving heads 30 (electric signals corresponding to the intensities of the fluorescence detected by the light receiving heads 30) into digital signals while controlling the light emission of the light source head 28 (the emission of the excitation light) and generates measurement data.

The measurement data that have been generated by the controller 52 are output at a predetermined timing to the image processing section 14. The image processing section 14 includes a computer in which a CPU, a ROM, a RAM, an HDD and the like are interconnected by a bus (none of these are shown). The image processing section 14 reads the measurement data that have been generated by the measurement section 12 and generates tomographic images (image data) of the specimen 18 based on the measurement data. A known configuration can be applied for the processing in the image processing section 14, so detailed description thereof will be omitted here.

In the optical tomographic measurement instrument 10, near-infrared light, whose wavelength has a peak between 700 nm and 1 μm, is used as the excitation light, and the light source head 28 emits the near-infrared light. Further, a fluorescent substance that emits fluorescence of a predetermined wavelength as a result of being irradiated with the near-infrared light is administered to the specimen 18 to be observed with the optical tomographic measurement instrument 10.

Here, as shown in FIG. 3 and FIG. 4, in the optical tomographic measurement instrument 10, a specimen holder 64 is used as a measurement object holder and a living body holder, and the specimen 18 is accommodated in the specimen holder 64. Further, in the optical tomographic measurement instrument 10, the specimen holder 64 is attached in the measurement section 12 so as to bridge the pair of arms 34.

Figure 1:
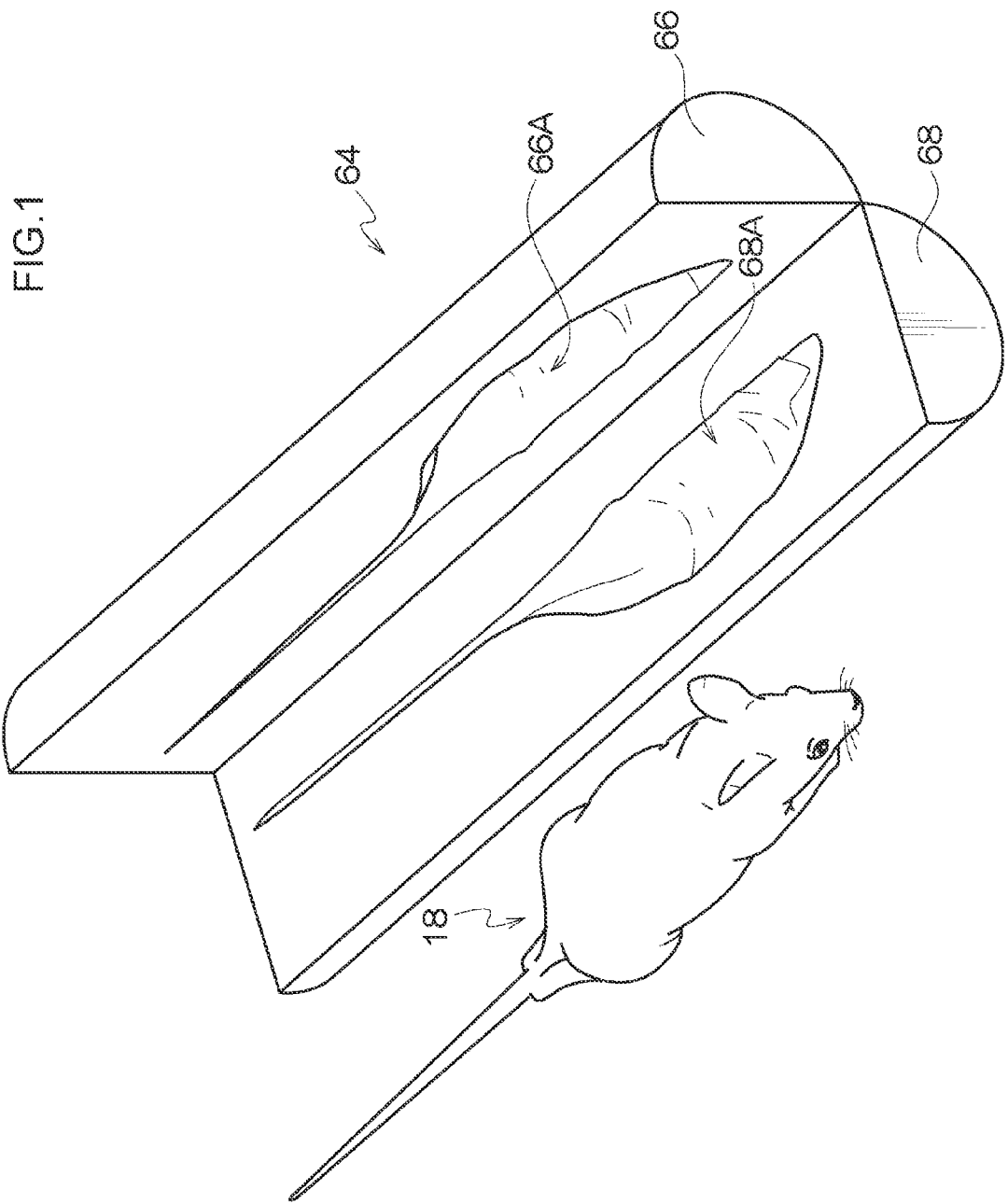
FIG. 1 is a schematic perspective view showing a state where a specimen (subject) holder pertaining to the present embodiment has been divided.
Figure 2:
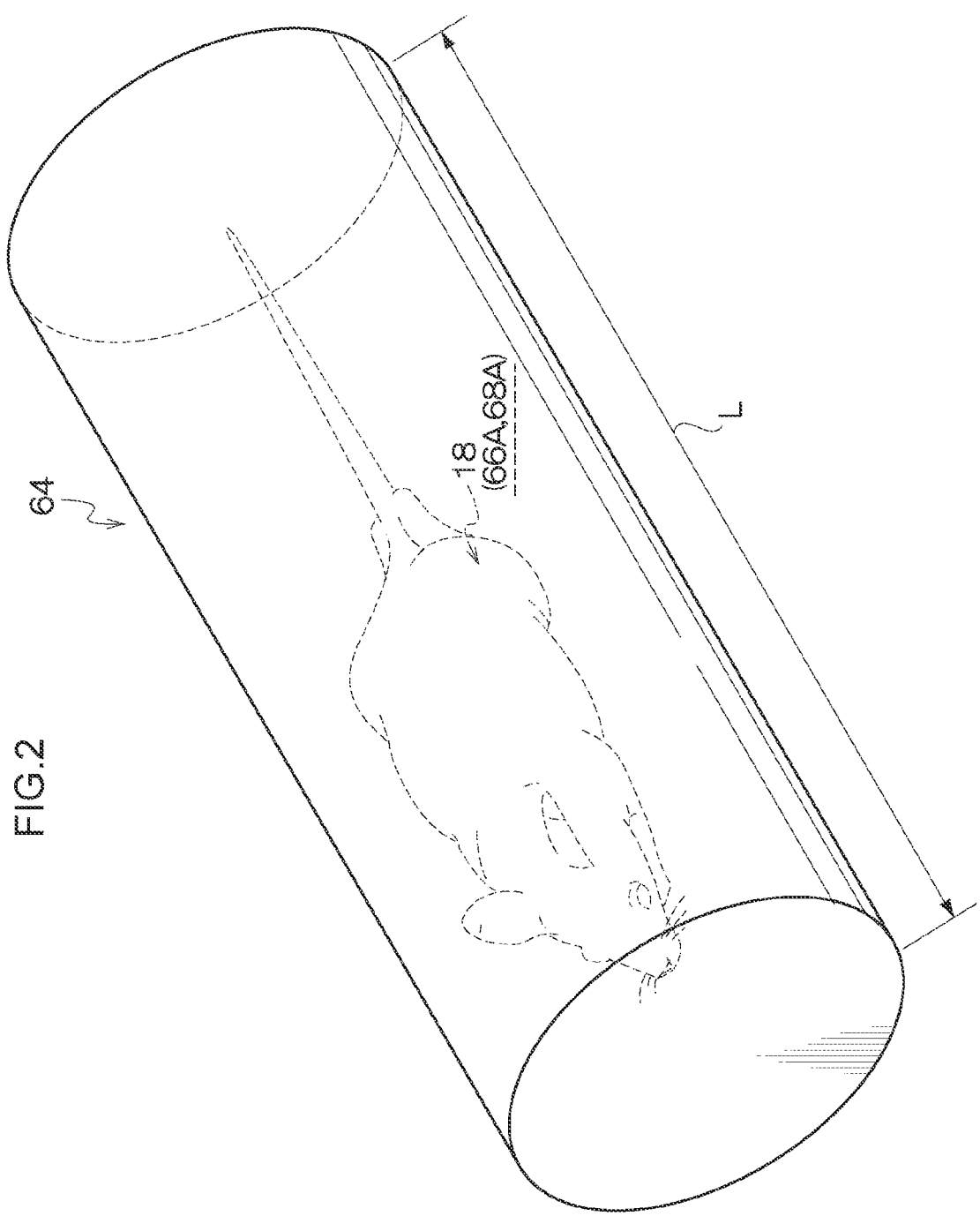
FIG. 2 is a schematic perspective view showing a state where a specimen is accommodated in the specimen holder.

As shown in FIG. 1, the specimen holder 64 is formed by two semicircular column-shaped blocks 66 and 68 and is formed in a cylindrical shape by putting together these blocks 66 and 68. That is, the specimen holder 64 applied to the present embodiment has a shape in which a cylindrical block is divided in two into the blocks 66 and 68 along a plane parallel to its axis.

Recessed portions 66A and 68A with inner shapes along (following) the outer shape of the specimen 18 accommodated inside the specimen holder 64 are formed in the blocks 66 and 68. That is, by putting together the blocks 66 and 68, a cavity portion having the inner shape substantially coincides with the outer shape of the specimen 18 is formed in the specimen holder 64 by the recessed portions 66A and 68A.

This, the specimen 18 is capable of being accommodated inside the specimen holder 64. Further, the epidermis of the specimen 18 accommodated inside the specimen holder 64 is made to be in close contact with the inner surfaces of the recessed portions 66A and 68A.

Here, the recessed portions 66A and 68A formed in the blocks 66 and 68 are formed so as to have inner shapes conforming to the original shape of the specimen 18 (the shape in a normal state). However, the recessed portions 66A and 68A may be given a shape slightly smaller than the specimen 18, for example, so that the specimen 18 is slightly compressed when the specimen 18 has been accommodated in the recessed portions 66A and 68A, or the epidermis of the specimen 18 may be made to be in close contact with the inner surfaces of the recessed portions 66A and 68A as a result of the accommodated specimen 18 being accustomed to the shape of the recessed portions 66A and 68A. Further, it suffices for the close contact between the specimen 18 and the recessed portions 66A and 68A to be in a range in which the scattering of light is not affected. In the present embodiment, for example, the body length direction of the specimen 18 coincides with the axial direction of the specimen holder 64, and the specimen holder 64 is divided in a plane along the body length direction of the specimen 18 accommodated inside the specimen holder 64. However, the position of the division is not limited to this and an arbitrary position can be set.

Inside the specimen 18, absorption and scattering occur with respect to the excitation light and the fluorescence. That is, the excitation light with which the specimen 18 has been irradiated and the fluorescence emitted from the fluorescent substance inside the specimen 18 pass through the specimen 18 while scattering and attenuating inside the specimen 18 and are emitted from the specimen 18.

Generally, a living body such as the nude mouse applied as the specimen 18 acts as an anisotropic scattering medium with respect to light. In an anisotropic scattering medium, forward scattering is dominant in a region until a light penetration length (an isotropic scattering length) is reached, but the scattering of light becomes isotropic in a region beyond the light penetration length (an isotropic scattering region). That is, in an anisotropic scattering medium, a wave property of incident light is maintained until the light reaches the light penetration length, but multiple scattering in which the deflection of light is random (isotropic scattering) occurs in the isotropic scattering region.

As for the transport equation of light (photons), which is a fundamental equation describing photon energy flow when light propagates while undergoing scattering inside a dense medium, a light diffusion equation is derived by approximating the scattering to isotropic scattering, and the solution of the reflected scattered light can be obtained using this light diffusion equation.

The optical tomographic measurement instrument 10 receives the fluorescence emitted from the fluorescent substance inside the specimen 18 and radiating around the specimen 18 and uses the light diffusion equation to acquire the distribution of the intensities of the fluorescence and the positions of the fluorescent substance inside the specimen 18. A known configuration can be employed for the computation using the light diffusion equation, so detailed description thereof will be omitted here.

Here, in the present exemplary embodiment, polyacetal resin (POM), which is an example of an anisotropic scattering medium and in which reduced scattering coefficient $\mu s'$ with respect to light is $1.05\ \mathrm{mm}^{-1}$, is used as the material forming the specimen holder 64 (the blocks 66 and 68). Further, as the blocks 66 and 68 of the specimen holder 64 contact the epidermis of the specimen 18 at the inner surfaces of the recessed portions 66A and 68A, it suffices for the blocks 66 and 68 to be formed in a thickness in which the excitation light scatters isotropically until it reaches the recessed portions 66A and 68A, that is, until the excitation light contacts the specimen 18 (i.e., a thickness equal to or greater than the light penetration length).

The reduced scattering coefficient $\mu s'$ is defined as $\mu s' = (1-g) \cdot \mu s$ from a scattering coefficient $\mu s$ and a parameter $g$ (a non-isotropic scattering coefficient) given as a cosine average in the scattering direction. The parameter $g$ is a value between pure backward scattering of $-1$ and forward scattering of $+1$, and a case where $g = 0$ represents isotropic scattering. Further, the light penetration length ($1/\mu s'$) with respect to an anisotropic scattering medium with no absorption corresponds to the reduced scattering length.

In a case where anisotropic scattering media are in contact with each other, when light that has propagated while undergoing repeated isotropic scattering in one of the anisotropic scattering media has been made incident on the other anisotropic scattering medium, the isotropic scattering state can be regarded as being substantially continued inside the other anisotropic scattering medium.

Therefore, the specimen 18 and the specimen holder 64 can be regarded as an integrated anisotropic scattering medium. If a gap exists between the specimen 18 and the blocks 66 and 68 of the specimen holder 64, there is the potential that isotropic scatterability cannot be maintained. However, in the present embodiment, as long as the gap exhibits a scattering state in a range where the error of the concentration distribution of the fluorescent substance obtained from the computation of a mathematical model based on the measurement data of the measurement section 12 falls within a predetermined allowable range, the specimen 18 and the blocks 66 and 68 are regarded as being in contact with each other.

Table 1 shows light penetration lengths (reduced scattering lengths) and reduced scattering coefficients $\mu s'$ by body tissues of the nude mouse serving as an example of the specimen 18 and of POM and silicon+$TiO_2$ serving as examples of materials of the blocks 66 and 68 with respect to light whose wavelength is 730 nm. Further, FIG. 6 shows reduced scattering coefficients with respect to reduced scattering lengths in the counter tissues and the materials.

TABLE 1

|  | Light Penetration Length (mm) | $\mu s'$ (1/mm) |
| --- | --- | --- |
| Lungs | 0.48 | 2.08 |
| Heart | 1.17 | 0.85 |
| Muscles | 2.97 | 0.34 |
| Skin | 0.5 | 2.02 |
| Liver | 1.61 | 0.61 |
| POM | 0.95 | 1.05 |
| Silicon + $TiO_2$ (16 mg/ml) | 0.71 | 1.4 |

Figure 6:
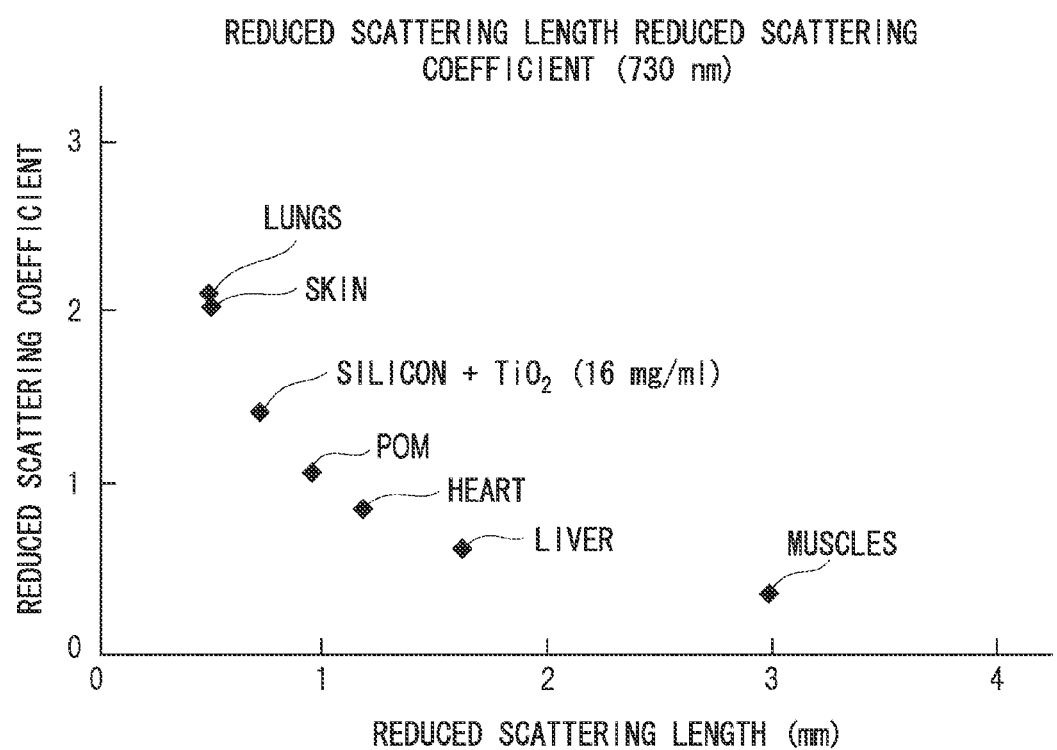
FIG. 6 is a chart showing reduced scattering coefficients with respect to reduced scattering lengths.

As shown in Table 1 and FIG. 6, in the specimen (nude mouse) 18, the reduced scattering coefficients $\mu s'$ have a range of $2.08\ \mathrm{mm}^{-1}$ to $0.34\ \mathrm{mm}^{-1}$. M25-34 Duracon resin, which is polyacetal resin, has a reduced scattering coefficient of $1.05\ \mathrm{mm}^{-1}$, and therefore this polyacetal resin can be used as the specimen holder 64.

Further, light scatterability can be given by dispersing titanium oxide ($TiO_2$) in silicon rubber, and light absorbability can be given by dispersing carbon (C) in silicon rubber. As shown in Table 1, for example, when about 16 mg/ml of titanium oxide ($TiO_2$) is included in silicon, a reduced scattering coefficient $\mu s'$ that is the same as that of the body tissues of the specimen 18 is obtained.

Therefore, the specimen holder 64 may, for example, be formed by mixing together, in a transparent two-liquid hardening silicon rubber such as Silpot 184 (trade name of Down Corning Toray Co., Ltd.), a titanium oxide powder such as cosmetics-use ultrafine titanium oxide serving as a scattering material and carbon black such as soot serving as an absorbing material.

The operation of the present embodiment will be described below.

When performing a measurement of the specimen 18 in the optical tomographic measurement instrument 10, the specimen 18 is accommodated in the specimen holder 64 and the specimen holder 64 is attached to the pair of arms 34 in the measurement section 12. At this time, the fluorescent substance is administered beforehand to the specimen 18.

In the measurement section 12, when the specimen holder 64 in which the specimen 18 is accommodated is attached, the moving motor 46 is driven, the specimen 18 is moved in the axial direction of the frame 26, and the light source head 28 and the light receiving heads 30 are caused to oppose a measurement site of the specimen 18. Then, in the measurement section 12, the light source head 28 is driven, the specimen 18 is irradiated with the excitation light, the fluorescence emitted from the specimen 18 on the basis of this excitation light is received by the light receiving heads 30 placed around the specimen 18, and thus one set of measurement data are acquired. Further, in the measurement section 12, the rotating motor 32 is driven and the frame 26 is rotated, whereby the light source head 28 is caused to oppose the next position of irradiation, the next position of irradiation is irradiated with the excitation light, and the next set of measurement data are acquired.

In the measurement section 12, by repeatedly moving the light source head 28 and the light receiving heads 30, the positions at which the specimen 18 is irradiated with the excitation light and the positions at which the fluorescence is received are relatively moved along a plane intersecting the body length direction of the specimen 18, and by performing a measurement corresponding to one circumnavigation around the specimen 18 on this plane (measurement plane), measurement data for obtaining one set of tomographic information (tomographic information in a predetermined position of the specimen 18) are acquired.

In the image processing section 14, upon measurement data corresponding to one circumnavigation around the specimen 18 are generated by the measurement section 12, the measurement data are read and predetermined data processing (image processing, tomographic reconstruction) is performed thereon. Thereby, the image processing section 14 obtains tomographic information (here, the concentration distribution of the fluorescent substance) with respect to the site of the specimen 18. The measurement section 12 can obtain tomographic information of multiple positions along the body length direction of the specimen 18 by moving the specimen 18 by the driving of the moving motor 46.

In a living body such as a nude mouse, the various organs are concentrated in the torso region, and in the case of measuring the concentration distribution of the fluorescent substance adhering to the organs and so forth, the torso region can be a measurement site. In this case, the specimen holder 64 is moved in the axial direction such that the torso region of the specimen 18 opposes the measurement plane of the frame 26. At this time, the movement of the specimen holder 64 may be stopped at multiple places along the body length direction of the specimen 18 (the axial direction of the specimen holder 64) and measurement data may be acquired at each of the stop positions, whereby tomographic information in multiple places along the body length direction of the specimen 18 can be obtained.

The measurement site with respect to the specimen 18 is not limited to the torso region of the specimen 18 and can be an arbitrary site that has been set in advance. It suffices to move the specimen holder 64 such that the set measurement site is made to oppose the axial center portion (measurement plane) of the frame 26.

In the measurement section 12, the specimen holder 64 having the outer shape in a cross section along the direction intersecting its axial direction is known, is used, and the specimen 18 is accommodated in the specimen holder 64. The specimen holder 64 is divisible into the two blocks 66 and 68 in a plane along its axial direction (e.g., a plane including its axial center), and the recessed portions 66A and 68A with inner shapes conforming to the outer shape of the specimen 18 are formed in the blocks 66 and 68.

Because of this, the accommodation of the specimen 18 in the specimen holder 64 is easy, and the specimen 18 accommodated in the specimen holder 64 is in close contact with the inner surfaces of the recessed portions 66A and 68A of the blocks 66 and 68.

Here, the measurement section 12 irradiates the outer peripheral surface of the specimen holder 64 with the excitation light. The excitation light propagates while scattering inside the specimen holder 64, and when the excitation light reaches the specimen 18, the excitation light propagates while scattering inside the specimen 18. Therefore, when the excitation light reaches the fluorescent substance administered inside to the specimen 18, the fluorescence is emitted from the fluorescent substance.

The fluorescence that has been emitted from the fluorescent substance in the specimen 18 propagates while scattering in the specimen 18, and when the fluorescence is emitted from the epidermis of the specimen 18, the fluorescence propagates while scattering in the specimen holder 64 (the blocks 66 and 68) and is emitted around from the outer peripheral surface of the specimen holder 64.

As described above, the optical tomographic measurement instrument 10 reconstruct the tomographic information representing the concentration distribution of the fluorescent substance inside the specimen 18 by performing an analysis using a mathematical model from the intensity distribution of the fluorescence emitted from the specimen 18.

Here, in the specimen holder 64 adopted in the present embodiment, the excitation light with which the specimen holder 64 has been irradiated from its outer peripheral surface scatters isotropically until the excitation light reaches the specimen 18. Because of this, the excitation light is made incident, while scattering isotropically, on the specimen 18 in contact with the surfaces of the recessed portions 66A and 68A of the blocks 66 and 68. Further, the fluorescence emitted from the fluorescent substance inside the specimen 18 is emitted from the epidermis while scattering isotropically, propagates while scattering isotropically inside the blocks 66 and 68 in contact with the epidermis, and is emitted from the outer peripheral face of the specimen holder 64.

In the specimen holder 64 in which the specimen 18 is accommodated, the blocks 66 and 68 are formed using an anisotropic scattering medium, and the specimen 18 is brought into close contact with and is accommodated in the recessed portions 66A and 68A of these blocks 66 and 68. Therefore, the specimen 18 and the specimen holder 64 can be regarded as an integrated anisotropic scattering medium having an identified outer shape.

Consequently, between the blocks 66 and 68 of the specimen holder 64 and the specimen 18, the excitation light and the fluorescence will propagate while isotropically scattering. Accordingly, the specimen 18 and the specimen holder 64 can be regarded as an integrated measurement object, and an analysis using a mathematical model can be performed based on the fluorescence emitted from the specimen holder 64.

That is, in a case in which the excitation light with which the specimen holder 64 has been irradiated does not exhibit isotropically scattering until it reaches the specimen 18, or in a case in which the fluorescence that has been emitted from the specimen 18 does not exhibit isotropically scattering when it is incident on the blocks 66 and 68, this does not conform to a mathematical model premised on isotropic scattering, so the precision of identifying the concentration distribution of the fluorescent substance will be poor and identification will be difficult.

In contrast, in the specimen holder 64, isotropic scattering of light is continued until the excitation light reaches the fluorescent substance in the specimen 18 and until the fluorescence emitted from the fluorescent substance in the specimen 18 is emitted from the specimen holder 64, so the precision of identifying the concentration distribution of the fluorescent substance by an analysis using a mathematical model does not drop.

When reconstructing the tomographic information of the specimen 18, measurement data corresponding to one circumnavigation with respect to the site is necessary. Further, in order to observe the movement and state of accumulation of the fluorescent substance that has been administered to the specimen 18, it is necessary to keep the specimen 18 alive. That is, when performing an observation of the specimen 18, sometimes the specimen 18 moves, and if the relative position of the fluorescent substance in the specimen 18 with respect to the frame 26 changes because of this, an adequate concentration distribution of the fluorescent substance cannot be obtained.

An anesthetic or the like can be administered to the specimen 18 in order to prevent the specimen 18 from ending up moving; however, when an anesthetic or the like is administered to the specimen 18, the muscles and the like of the specimen 18 relax and the specimen 18 becomes unable to keep its original shape. In accompaniment with this, not just the organs in the specimen 18 but also the fluorescent substance in the specimen 18 will also move.

In this state, even if the concentration distribution of the fluorescent substance of the specimen 18 is obtained, identification of the relative positions of the organs in the specimen 18 and the relative positions between the organs and the fluorescent substance will be difficult.

Here, in the specimen holder 64, the recessed portion 66A of the block 66 and the recessed portion 68A of the block 68 are formed in inner shapes corresponding to the original outer shape of the specimen 18 (the outer shape in a steady state, i.e., the body shape), and the specimen 18 is accommodated inside these recessed portions 66A and 68A. Therefore, even if an anesthetic is administered to the specimen 18 and the specimen 18 relaxes, the outer shape of the specimen 18 can be kept in its original shape, and changes in the positions of the organs can also be controlled.

Consequently, by using the specimen holder 64, a concentration distribution of the fluorescent substance in the specimen 18 can be obtained in a state in which the specimen 18 is kept alive and the organs in the specimen 18 are at adequate relative positions.

Moreover, the specimen holder 64 is divisible (can be separated) into the blocks 66 and 68, and the accommodation and removal of the specimen 18 can be performed by dividing the specimen holder 64. For this reason, when a measurement of one specimen 18 is completed and a measurement of the next specimen 18 is to be performed, the specimen 18 can be smoothly replaced.

Because of this, in the optical tomographic measurement instrument 10, measurements with respect to numerous specimens 18 can be performed in a short amount of time, and throughput can be remarkably improved compared to a case in which, for example, the specimen 18 is immersed in a solution and measured.

In this way, by using the specimen holder 64 that is formed in a predetermined outer shape by a material that conforms to the optical properties of the specimen 18 such as its absorption coefficient µa and its reduced scattering coefficient µs' and in which light isotropically scatters, and by forming inside the specimen holder 64 the cavity portion (the recessed portions 66A and 68A) conforming to the outer shape of the specimen 18, adequate optical tomographic information of the specimen 18 (the concentration distribution of the fluorescent substance) can be smoothly obtained.

In the optical tomographic measurement instrument 10, when unnecessary light not originating in the fluorescent substance that is the measurement object is incident on the light receiving heads 30, error arises in the measurement data. For this reason, the following consideration is made when deciding the fluorescent substance, the wavelength of the excitation light emitted from the light source head 28, and the material of the specimen holder 64 (the blocks 66 and 68).

The wavelength band of light that transmits well in a living body such as the specimen 18 is 700 nm to 1100 nm. Accordingly, a fluorescent substance that emits fluorescence in this wavelength region is used as the fluorescent substance (fluorescent labeling agent) administered to the specimen 18. Examples of such fluorescent substance include Alexa Flour 750 (trade name of Life Technologies Japan), for example, and this fluorescent substance will be taken as an example in the following description. This fluorescent substance has a light absorption peak wavelength of about 750 nm and efficiently gives off fluorescence because of excitation light whose wavelength is 720 nm to 750 nm.

Figure 7:
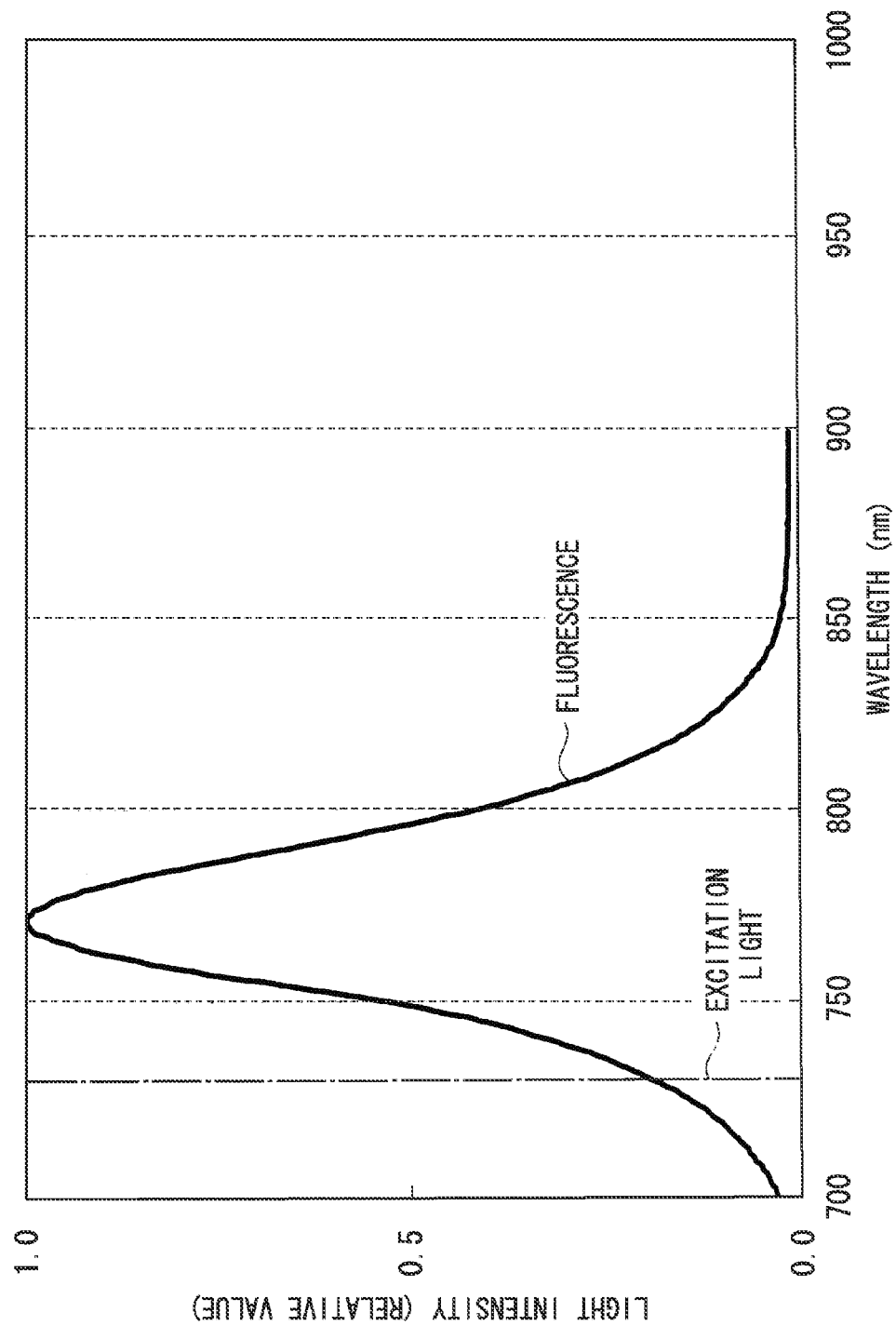
FIG. 7 is a diagram showing an example of a spectral property of fluorescence that a fluorescent substance emits with respect to excitation light.

FIG. 7 shows the normalized spectral property (light intensity with respect to wavelength) of the fluorescence of the fluorescent substance with respect to the excitation lightstate. A semiconductor laser having emission wavelength of 730 nm is adopted as the light source of the excitation light.

As shown in FIG. 7, the fluorescence that the fluorescent substance gives off with respect to the excitation light with a 730 nm wavelength has a peak wavelength of about 770 nm and a half width of 50 nm.

The reasons a semiconductor laser is used for the light source that emits the excitation light are because the wavelength band region is narrow (i.e., it has monochromaticity) and the semiconductor laser exhibits a large peak light intensity in a narrow band.

However, if the excitation light emitted from the semiconductor laser is monochrome (if the wavelength band region is narrow), it is necessary to consider Raman scattered light caused by the material of the specimen holder 64. Raman scattered light is a phenomenon in which some of incident light collides with molecules and atoms configuring a material and energy transfer takes place, whereby light with a wavelength different from that of the incident light is scattered. Most of the incident light keeps its energy and propagates as light with the same wavelength even when it collides with the molecules and atoms configuring a material.

In the present exemplary embodiment described above, polyacetal resin (called POM below), which is an anisotropic scattering medium conforming to the optical properties of the specimen 18, is used as the material of the specimen holder 64 (the blocks 66 and 68).

FIG. 8 shows the spectral property (light intensity with respect to wavelength) of the fluorescence emitted from the fluorescent substance excited by the semiconductor laser having emission wavelength of 730 nm in the dashed line, and the spectral property (light intensity with respect to wavelength) of the Raman scattered light given off from the POM in the solid line. Each of the shown spectral properties is normalized.

As shown in FIG. 8, it will be understood that the Raman scattered light in the POM has multiple peaks (local maximums) in a wavelength band region equal to or greater than 750 nm. Further, one of the peak wavelengths of the Raman scattered light in the POM comes close to the peak wavelength of the fluorescence given off from the fluorescent substance, and the interval between them is about 10 nm in wavelength.

Here, it is necessary to detect fluorescence by separating the Raman scattered light in the POM so that noise is not included in the spectrum (light intensity) of the fluorescence to be measured. It is common to use optical filters as described below for this separation.

Optical filters (not shown) are placed on the light incident sides of light receiving elements (not shown) of the light receiving heads 30. FIG. 9 shows the spectral properties (light transmittance with respect to wavelength) of the optical filters applied in the present exemplary embodiment.

In the light receiving heads 30, high pass interference filters, colored glass filters, and low pass interference filters are disposed as the optical filters. The high pass interference filters have the property of transmitting light of long wavelength bands and blocking the transmission of light of short wavelength bands. In the light receiving heads 30, these high pass interference filters are used to remove the excitation light. The high pass interference filters function as excitation light cutting filters that remove the excitation light and transmit light with wavelengths longer than that of the excitation light.

In the light receiving heads 30, the colored glass filters are used for the purpose of supplementarily cutting the excitation light. The colored glass filters block the transmission of the excitation light that has not completely removed by the high pass interference filters.

The low pass interference filters have the property of transmitting light of short wavelength bands and blocking the transmission of light of long wavelength bands. In the light receiving heads 30, the low pass interference filters are used to remove light of wavelength bands shorter than that of the fluorescence, that is, the Raman scattered light. The low pass interference filters function as Raman scattered light cutting filters that transmit light with short wavelengths including the fluorescence and block the transmission of light with wavelengths longer than that of the fluorescence.

Here, low pass interference filters including the following two functions are used for the low pass interference filters for effectively removing the Raman scattered light. One is removing the spectrum of the peak wavelength of the Raman scattered light in the POM close to the peak wavelength of the fluorescence in the interval of about 10 nm, and this is realized by appropriately setting the half width of the low pass interference filters. The other is removing the Raman scattered light of wavelength bands equal to or greater 900 nm, in which the spectrum of the fluorescence does not exist, and this can be realized by the stop-band (the band that does not transmit light) of the low pass interference filters.

Consequently, as long as the difference between the wavelength (peak wavelength) of the fluorescence given off from the fluorescent substance and the peak wavelength of the Raman scattered light is a difference that can be regarded as having had the component of the Raman scattered light removed from the spectrum of the fluorescence by the optical filters, noise caused by the Raman scattered light can be prevented from affecting the measurement data.

However, if the peak wavelength of the fluorescence and the peak wavelength of the Raman scattered light are close to each other and the fluorescence and the Raman scattered light being substantially superimposed, it is difficult for the Raman scattered light to be separated and removed by the optical filters. That is, if the peak wavelength of the fluorescence and the peak wavelength of the Raman scattered light are apart (different), it is possible to separate and remove the Raman scattered light by the combination of the optical filters, control the Raman scattered light, and extract the fluorescence that can be substantially regarded as not including the component (noise component) of the Raman scattered light. However, if the peak of the fluorescence and the peak of the Raman scattered light are superimposed, it is difficult to separate and remove the Raman scattered light with the combination of the optical filters.

The peak wavelength of the Raman scattered light shifts (changes) depending on the wavelength of the transmitted light (the excitation light of the fluorescent substance) and the molecular structure of the material through which the light is transmitted. Further, the peak wavelength of the fluorescence that the fluorescent substance gives off is not dependent on the wavelength of the excitation light.

Accordingly, by setting the wavelength of the excitation light to a relatively longer wavelength, the peak wavelength of the Raman scattered light can be separated from the peak wavelength of the fluorescence that the fluorescent substance gives off. Thereby, the Raman scattered light can be separated from the peak wavelength of the fluorescence by the low pass interference filters. At this time, since the peak wavelength of the excitation light and the peak wavelength of the fluorescence become closer to each other, the properties of the aforementioned high pass interference filters and colored glass filters may be reconfigured, if needed.

In the present exemplary embodiment, POM (polyacetal resin) is used as the material of the specimen holder 64. However, examples of materials having the same optical properties as those of POM include polyethylene (PE), and polyethylene can be also used as the material of the specimen holder 64.

FIG. 10 shows the spectral property (light intensity with respect to wavelength) of the fluorescence given off from the fluorescent substance that has been excited by the semiconductor laser whose emission wavelength is 730 nm by the dashed line, and the spectral property (light intensity with respect to wavelength) of the Raman scattered light given off from the polyethylene by the solid line. The Raman scattered light in the polyethylene is shown as a relative intensity with respect to the maximum intensity of the Raman scattered light in the POM shown in FIG. 8 that has been normalized as 1.

As shown in FIG. 10, when light with a wavelength of 730 nm is used as the excitation light, the Raman scattered light that the polyethylene gives off has a remarkably small intensity at a wavelength near 780 nm in the POM (see FIG. 8). Further, the peak wavelength of the Raman scattered light exceeds 800 nm (about 810 nm) even that is close to the peak wavelength of the fluorescence, and therefore, it is easy to separate the peak wavelength of the Raman scattered light from the peak wavelength of the fluorescence by using optical filters (low pass interference filters).

By making the specimen holder 64 (the blocks 66 and 68) using polyethylene which has such optical property, detection of the Raman scattered light by the light receiving heads 30 can be controlled. Accordingly, in the measurement section 12 of the optical tomographic measurement instrument 10, measurement data with which more adequate tomographic image reconstruction can be obtained compared to the case of using the specimen holder 64 formed by POM.

Here, in order to control the detection of the Raman scattered light, polyethylene, in which the peak wavelength of the Raman scattered light is apart from the peak wavelength of the fluorescence, has been taken as an example and described. However, the material of the specimen holder 64 is not limited to this, and an arbitrary material can be applied as long as it is an anisotropic scattering medium conforming to the optical properties of the specimen 18 and in which the Raman scattered light does not become a noise component when the fluorescence is detected by the light receiving heads 30.

As described above, methods of controlling the noise component caused by the Raman scattered light on the measurement data include changing only the wavelength of the excitation light and changing only the material of the specimen holder 64. However, the methods are not limited to these and an appropriately combination of the wavelength of the excitation light, the fluorescent substance, and the material of the specimen holder 64 may be chosen so that the peak wavelength of the Raman scattered light is apart from the peak wavelength of the wavelength of the fluorescence.

In this way, by choosing the material of the specimen holder 64 such that the peak wavelength of the Raman scattered light is apart from the wavelength of the fluorescence and controlling the effect that the Raman scattered light has on the intensity of the fluorescence received by the light receiving heads 30, measurement error caused by the Raman effect is prevented from arising and measurement data with which high-precision tomographic image reconstruction can be performed are obtained.

In the present exemplary embodiment described above, the recessed portions 66A and 68A that integrally accommodate the specimen 18 that is a living body of a measurement object has been formed However the present invention is not limited to this and it suffices for the present invention to have a configuration in which is formed a cavity portion that is capable of accommodating at least a predetermined site including a measurement site of the measurement object (living body) without changing the original outer shape of the site or the basic positions of the tissue inside the site.

In this case, in the present embodiment, the block is divided into a plurality to accommodate the measurement object. However, the present invention is not limited to this and, for example, the cavity portion inside the block may be opened outward, and the measurement site of the specimen may be held inside the holder by inserting the measurement site inside the cavity portion of the block through this opening.

Further, although the present embodiment has been described using the specimen holder 64 whose outer shape is a cylindrical shape, as long as the measurement object holder and the living body holder according to the present invention have outer shapes that are defined beforehand, arbitrary outer shapes can be applied. In this case, it is preferable for the cross-sectional area and shape along the axial direction of the frame 26 of the outer shape to be constant, for example a prismatic shape such as a square or a cross-sectionally elliptical shape. In this manner, the outer shape (cross-sectional shape) does not change even when the measurement position has been moved, and arithmetic processing when reconstructing the cross-sectional area is easy.

Moreover, in the present embodiment, since the position at which the measurement object is irradiated with the excitation light is configured to be changed in twelve stages at 30° steps, the measurement object holder and the living body holder can also be a regular dodecagon prism (where the outer shape in the cross section along a direction intersecting the body length direction of the specimen 18 is a regular dodecagon). At this time, the lengthwise direction of the measurement object holder and the living body holder are formed so as to coincide with the body length direction of the living body. Thereby, each of the flat faces can be irradiated with the excitation light, and the fluorescence emitted from each of the flat faces can be detected.

Further, the present exemplary embodiment has been described taking a small animal such as a nude mouse as the measurement object, but the present invention can be applied to arbitrary vertebrate animals such as mammalian animals as living bodies taken as the measurement object. It suffices for the measurement object holder to enable a living body taken as the measurement object or a specific site (measurement site) of a living body taken as the measurement object to be held in its original shape. Further, it suffices for the measurement object holder and the cavity portion formed inside the measurement object holder to enable at least a measurement site of a living body taken as the measurement object to be held in its original state.

The present embodiment has been described using the optical tomographic measurement instrument 10, but the measurement object holder and the living body holder of the present invention are not limited to this and can be applied to an optical measurement instrument of an arbitrary configuration that takes a living body such as the specimen 18 as a measurement object and performs various measurements using light with which the measurement object has been irradiated and measurements using light that has been emitted from inside the measurement object.

The invention claimed is:

1. A measurement object holder that holds a measurement object in an optical measurement instrument, wherein the optical measurement instrument takes, as the measurement object, a living body in which isotropic scattering of light occurs inside and receives light emitted from the measurement object, the measurement object holder comprising:
   a block that is formed in a predetermined outer shape by a material having optical properties in which the isotropic scattering of light occurs inside; and
   a cavity portion that is formed inside the block, that has an inner shape following the outer shape of the measurement object and in which the measurement object is accommodated.

2. The measurement object holder according to claim 1, wherein the block is formed in a cylindrical shape, and the cavity portion is formed such that a length direction of the measurement object is along an axial direction of the block.

3. The measurement object holder according to claim 1, wherein the block is divided into a plurality of sections by a plane passing through the cavity portion.

4. The measurement object holder according to claim 1, wherein the cavity portion is formed so as to at least accommodate a site set as a measurement site in the measurement object.

5. A living body holder comprising a block that is formed in a predetermined outer shape by a material having optical properties in which isotropic scattering of light occurs inside, the block being formed with a cavity portion inside the block having an inner shape that follows an outer shape of a living body in which isotropic scattering of light occurs inside, and the living body being held in the block by the living body being accommodated inside the cavity portion.

6. The living body holder according to claim 5, wherein the block is formed in a cylindrical shape, and the cavity portion is formed such that an axial direction of the block is along a length direction of the living body.

7. The living body holder according to claim 5, wherein the block is divided into a plurality of sections by a plane passing through the cavity portion.

8. An optical measurement instrument comprising:
the living body holder according to claim 5, wherein the living body holder accommodates a living body to which has been administered a fluorescent substance that emits fluorescence as a result of being irradiated with excitation light;
holding portions that hold, at both end portions in a length direction of the living body, the block of the living body holder in which the living body is accommodated;
a light source head that irradiates, with the excitation light, the living body inside the block held by the holding portions; and
a light receiving head that receives the fluorescence emitted from the fluorescent substance inside the living body due to the irradiation of the excitation light from the light source head.

9. The optical measurement instrument according to claim 8, wherein a wavelength of the excitation light, the fluorescent substance, and the material of the block are set such that a wavelength of the fluorescence and a local maximum of a wavelength of Raman scattered light differ by a predetermined wavelength or more, on the basis of the wavelength of the excitation light determined per fluorescent substance, the wavelength of the fluorescence, and the wavelength of the Raman scattered light emitted from the block due to the Raman effect occurring inside the block as a result of the block being irradiated with the excitation light.

10. The optical measurement instrument according to claim 9, wherein the predetermined wavelength separating the wavelength of the fluorescence and the local maximum of the wavelength of the Raman scattered light is a wavelength determined based on the spectral properties of an optical filter disposed in the light receiving head.

\* \* \* \* \*